United States Patent [19]

DuRoss

[11] Patent Number: 5,023,092
[45] Date of Patent: Jun. 11, 1991

[54] MANNITOL HAVING GAMMA SORBITOL POLYMORPH

[75] Inventor: James W. DuRoss, Smyrna, Del.

[73] Assignee: ICI Americas Inc., Wilmington, Del.

[21] Appl. No.: 352,632

[22] Filed: May 12, 1989

Related U.S. Application Data

[63] Continuation-in-part of Ser. No. 207,679, Jun. 16, 1988, abandoned.

[51] Int. Cl.$^5$ .................. A23L 1/22; A23L 1/236; A23G 3/30; A23G 1/00
[52] U.S. Cl. .......................... 426/3; 426/660; 426/658; 426/804; 426/454; 426/650; 426/656; 127/29; 568/852; 568/863; 568/868
[58] Field of Search ............... 426/660, 656, 658, 3, 426/804, 454; 127/29; 260/635; 424/176; 568/852, 863, 868

[56] References Cited

U.S. PATENT DOCUMENTS

| | | | |
|---|---|---|---|
| 3,484,492 | 12/1969 | Hales | 260/635 |
| 4,252,794 | 2/1981 | DuRoss | 424/176 |
| 4,408,041 | 10/1983 | Hirao et al. | 426/658 |
| 4,507,511 | 3/1985 | Reiff et al. | 426/548 |
| 4,605,794 | 8/1986 | Reiff et al. | 568/852 |
| 4,725,387 | 2/1988 | Hirao et al. | 426/804 |

Primary Examiner—Jeanette Hunter
Attorney, Agent, or Firm—William E. Dickheiser

[57] ABSTRACT

Mannitol having the crystalline form of gamma sorbitol is made by co-crystallizing relatively high mannitol containing sorbitol melt in a twin screw mixer. Tablets, chocolate and chewing gum made with the co-crystallized product offer improvements similar to those realized with pure crystalline components.

10 Claims, No Drawings

MANNITOL HAVING GAMMA SORBITOL POLYMORPH

This is a continuation-in-part of co-pending application Ser. No. 07/207,679 filed June 16, 1988, now abandoned.

The present invention is directed to mannitol and sorbitol crystalline modifications. Specifically, it is directed to gamma sorbitol having co-crystallized therewith mannitol in the gamma sorbitol polymorph. In particular, it is a co-crystalline product derived from a dehydrated aqueous solution of sorbitol containing mannitol. It is further directed to improved confections such as chewing gum, edible tablets and chocolates.

Attempts to crystallize a molten mixture of sorbitol containing from 5-35 weight percent mannitol employing a conventional process such as the spray-melt seed process yields a variation in products having mixed polymorphs of mannitol and sorbitol including substantial amounts of amorphous noncrystalline product. Because of the high concentration of mannitol, the product resulting therefrom is tacky, has a very low heat of fusion and melting point and results in a material which is only 20-60 percent crystallized depending upon the mannitol concentration. Because of the high concentrations of mannitol, it is difficult to cool the molten crystallizing mass at an appropriate rate to permit the formation of a uniform crystalline product. This product is not useable in that most grinding equipment is jammed with "glassy" product usually found in it. Such a material has no known utility because it cannot be converted to a pulverized product for use in applications where a dry, free flowing, non-hygroscopic crystalline product is needed.

The co-crystallized mannitol containing sorbitol of the invention is characterized by chromatography as a product having 5-35 percent by weight mannitol and an X-ray diffraction pattern typical of gamma sorbitol. The material has an X-ray diffraction pattern typical of gamma sorbitol as shown in Table I entitled "X-ray Diffraction Measurements". The table also shows as a means for comparison the X-ray diffraction data for pure crystalline mannitol.

TABLE I
COMPARISON OF X-RAY DIFFRACTION MEASUREMENTS

| Gamma Sorbitol (100%) | | Example 1 | | Mannitol (100%) | |
|---|---|---|---|---|---|
| *d | **I/I* | d | I/I* | d | I/I* |
| 9.44 | 14 | 9.39 | 7 | | |
| 8.72 | 12 | 8.70 | 5 | 8.51 | 22 |
| 7.55 | 39 | 7.75 | 23 | 7.77 | 3 |
| 7.49 | 35 | 7.49 | 68 | | |
| 6.87 | 9 | | | | |
| 6.34 | 11 | 6.35 | 14 | | |
| 6.00 | 26 | 6.00 | 23 | 6.09 | 43 |
| 5.97 | 23 | 5.98 | 21 | | |
| 5.77 | 9 | | | | |
| 5.64 | 8 | | | | |
| 5.42 | 9 | | | | |
| 5.20 | 21 | 5.20 | 18 | 5.32 | 11 |
| 5.11 | 26 | 5.11 | 15 | | |
| 5.02 | 33 | 5.01 | 23 | | |
| 4.73 | 100 | 4.72 | 100 | 4.75 | 90 |
| 4.51 | 11 | 4.53 | 22 | 4.54 | 2 |
| 4.39 | 26 | 4.38 | 12 | 4.36 | 18 |
| 4.33 | 50 | 4.33 | 50 | 4.23 | 39 |
| 4.15 | 15 | 4.13 | 19 | 4.12 | 8 |
| 4.04 | 61 | 4.04 | 55 | | |
| 3.91 | 53 | 3.91 | 52 | | |
| 3.76 | 30 | 3.77 | 29 | 3.81 | 100 |
| | | 3.66 | 8 | 3.62 | 7 |
| 3.54 | 38 | 3.52 | 24 | | |
| 3.50 | 50 | | | | |
| 3.49 | 67 | 3.48 | 64 | | |
| 3.48 | 38 | | | 3.45 | 10 |
| | | 3.39 | 33 | 3.37 | 4 |
| 3.30 | 30 | 3.29 | 21 | | |
| 3.07 | 18 | 3.06 | 21 | | |
| 3.04 | 18 | 3.04 | 15 | 3.04 | 30 |
| 2.95 | 9 | | | | |
| 2.946 | 6 | 2.911 | 5 | 2.937 | 1 |
| | | | | 2.858 | 5 |
| 2.820 | 23 | 2.819 | 18 | 2.824 | 10 |
| | | 2.790 | 22 | 2.747 | 5 |
| 2.643 | 38 | 2.641 | 31 | 2.677 | 24 |
| | | | | 2.618 | 5 |
| 2.558 | 21 | 2.548 | 13 | 2.576 | 3 |
| 2.427 | 18 | 2.421 | 5 | 2.500 | 8 |
| 2.346 | 8 | 2.321 | 4 | 2.332 | 22 |
| 2.271 | 11 | 2.264 | 10 | 2.254 | 3 |
| 2.240 | 12 | 2.229 | 8 | | |
| 2.179 | 17 | 2.181 | 7 | 2.167 | 4 |
| | | 2.127 | 10 | 2.114 | 3 |
| | | 2.058 | 10 | 2.057 | 20 |
| | | 1.994 | 7 | 2.003 | 5 |
| | | 1.973 | 8 | 1.931 | 5 |
| | | | | 1.902 | 4 |

*d = d-spacings; interlayer spacings; anstroms
**I/I* = Intensity values of individual peaks The mannitol content is determined in conventional gas/liquid chromatography analytical equipment or high pressure liquid chromatography techniques.

The co-crystallized product may further be characterized as having a melting point from 90°-100° C. as determined by differential scanning calorimetry. Surprisingly, the curves generated in the apparatus indicates a single peaked melting range unlike the double peak found for a synthetic blend made by pulverizing pure mannitol with pure sorbitol crystals into a uniform mixed powder or by blending a molten mixture of the two. This indicates that the product is a single crystal of sorbitol with mannitol included and not a mixture of pure crystals of mannitol and sorbitol.

In my earlier patents, U.S. Pat. No. 3,973,041 and U.S Pat. No. 4,252,794, I have described procedures for crystallizing pure sorbitol into crystals suitable for manufacturing chewing gum and hard tablets. In general, these processes employ a mechanical mixing device wherein molten sorbitol is simultaneously cooled and kneaded into a magma containing crystals which are and thereafter passed through an extrusion plate to form elongated shapes of varying cross-sectional dimensions ranging from 3 millimeters up to 50 millimeters. These shapes are immediately quenched in cold fluids or room temperature air and permitted to crystallize slowly for a period of several days. The preferred type of mixer is a continuous dual shaft twin bladed mixer of the intermeshing type. Mixers of this type are discussed in "Chemical Engineers Handbook", fifth Edition, editing by R. H. Perry and C. H. Chilton (1973), pages 19-21. Characteristics of these mixers are that they include intermeshing kneading blades mounted on two parallel shafts which rotate in the same direction at the same speed with close blade-to-wall and blade-to-blade clearances. A preferred continuous mixer is the high-sheer Readco Continuous Processor made by Teledyne Readco of York, Pa. This mixer is shown and described in U.S. Pat. Nos. 3,419,250 and 3,618,902. Other high, sheer continuous twin screw mixers which might be employed at low shaft speed include the Baker Perkins Multi-Purpose (M-P) Mixer made by Baker Perkins, Inc., of Sagnaw, Michigan and the ZSK Twin Screw Compounding Extruder made by Werner & Pfleiderer Corporation of Stuttgart, Germany. The Baker Perkins mixer is shown in U.S. Pat. Nos. 3,195,868 and 3,198,491. Alternative blade configurations which can be used in mixers of this type are shown in U.S. Pat. Nos. 3,423,074 and 3,490,750. These mixers are commercially available in varying sizes from Teledyne Readco having kneader blade diameters of 2, 5, 15, and 24 inches and optional feed and/or discharge screw auxiliaries. These devices are supplied with discharge nozzles and extrusion plates which permit the discharge of varying cross-sections and shapes from the mixer. I have now found that this equipment can be used to crystallize dehydrated high mannitol and sorbitol solutions resulting from the aqueous mannitol crystallization process.

The melting point for pure mannitol is 166° C. while that of pure sorbitol is 102° C. In moving from pure sorbitol to pure mannitol, a eutectic mixture containing 9-12 percent mannitol occurs at 25° C. In concentrations ranging from about 5 to 35% by weight of mannitol in sorbitol, the melting points can vary from 50°-150° C. depending upon crystallization techniques. Therefore, the starting temperature of the molten starting material employed in the crystallization can vary with concentration of mannitol. In commonly occurring mannitol containing sorbitol blends the mannitol content ranges from about 7-16 percent.

In general, three sources are available for the aqueous mannitol-containing sorbitol solutions used as starting material. One source is derived from invert sugar which is a 50-50 mixture of glucose and fructose which is hydrogenated in the presence of nickel catalysts to form a saturated solution of sorbitol/mannitol in a 3/1 molar ratio. The supernatant liquid remaining after the fractional crystallization of mannitol from the solution normally contains from 7-16 percent mannitol. This mannitol-rich solution can then be dehydrated to form a starting material containing 99.8 percent by weight solids.

Another method for preparing starting material involves the epimerization of dextrose to form a product which contains about 30 percent manose which, when hydrogenated, produces mannitol. The mannitol-rich solution can then be fractionally crystallized to form a starting material as outlined above.

Another practical method for making mannitol is developed from the hydrogenation of high fructose corn syrup as, for example, one having a DE(dextrose equivalent) of 63 or thereabouts. The resulting hydrogenated syrup is treated by the removal of mannitol by crystallization as outlined above. Any of these starting materials can then be melted and held in a feed tank for further crystallization in the process.

In carrying out the crystallization, the molten blend containing about 5-35 percent and more often, 7-16 percent mannitol (0.05 to less than 1.0% moisture) is held in a feed tank in a relatively dry atmosphere to inhibit moisture pickup such that the moisture content does not exceed about 0.75 percent by this precaution becomes less a factor as the temperature of the molten mixture exceeds 100° C. In the operation of the mixing equipment the feed rate is adjusted such that as the cooling magma passes through the mixer, a molten blend having increasing concentrations of crystals is generated as the magma passes through from the feed to the discharge orifice. The rotating screws move the molten magma containing crystals from the center of the equipment to the outer cooled edge whereupon additional crystals are precipitated and remixed with additional molten material to act as a co-crystallized seed. As the temperature profile drops from molten feed temperature to discharge temperature the viscosity of the melt increases due to the formation of mannitol/sorbitol co-crystals in concentrations ranging from 35-80 percent by weight. The action of the rotating screws pushes the molten magma containing crystalline mass in the form of a rope or ribbon paste through the discharge orifice whereupon it is extruded as an elongated mass in the shape of a ribbon, circular rod, oval rod, hexagonal rod, or star-shaped rod into the cold zone. It is cut into short lengths ranging from 1 to 4 inches and permitted to cool for several days at room temperature. If the temperature of the emitted extrudate is too hot the molten mass will not retain its shape and is difficult to handle. When such operating conditions take place, the product obtained is a mixture of crystals with glass. The problem can be corrected by decreasing the throughput time or jacket cooling temperature or a combination of both. Under ideal operating conditions, the extrudate crystalline paste develops a solid outer shell of crystalline product which is only slighted wetted on the interior side with molten magma. This material when permitted to stand will fully crystallize if allowed to cool slowly for a period of 6-96 hours for an extrudate having a cross-sectional dimension of about 5-20 millimeters. Longer periods may be required ior extruded shapes having a cross-sectional dimension of greater than 20 millimeters.

The manufacture of the co-crystallized mannitol/sorbitol product may be better understood with reference to the following example wherein all proportions expressed therein are by weight unless otherwise specified.

EXAMPLE 1

Molten sorbitol containing about 10% by weight mannitol and 0.2% moisture was fed at a temperature of 95° C. continuously into a Readco Continuous Mixer similar to that described in U.S. Pat. No. 3,618,902 and having 24 inch diameter dual mixing blades. The mixer was operated under continuous steady state conditions with an output rate ranging from 1950-2025 pounds per hour. The cooling jacket temperature was held at 25° C. with a shaft rotating speed of 10.5 rpm. The effluent nozzle water temperature varied from 86°-88° C. The crystalline paste discharge was passed through a foraminous spinnerette having cylindrical openings of 12 millimeters. The extrudate was allowed to settle on a moving belt in an atmosphere of cool air and after cooling for one minute, was cut into 2 inch lengths and thereafter placed in storage trays and permitted to stand at room temperature in a dry room for a period of three days. The material was ground to a particle size of −20/+60 mesh U.S. sieve series average particle size 200-300 microns. Upon examination, the material had needlelike loose disrupted crystals Upon analysis by GLC, it was found to be 85.99% sorbitol, 10.01% mannitol, 0.45% 1,4 sorbitan, 0.67% hexitan and 0.72% total isomers. The X-ray diffraction spectra for the material was like that spectra shown in Table I for the co-crystallized material having a spectra exhibited by gamma sorbitol. Various samples collected during the manufacturing run had melting points ranging from 95-°C.-98° C. with a heat of fusion ranging from 35-42 calories per gram. The curve obtained by Differential Scanning Calorimetry (DSC) indicates a single phase melt transition point characteristic of gamma sorbitol. Scanning Electron Micrographic examination at 2000× magnification shows individual crystals to have widths of about 1.0 micron and above: however, some runs vary from 0.5-1.5 microns and above. Tablets of this material can be compressed to a Strong Cobb Arner Hardness value of about at least 18-20 kgs.

Confectionary compositions such as hard candy according to the invention may be prepared by compounding the mannitol/sorbitol co-crystals of the invention with flavoring agents and/or other additives such as adjuncts, artificial sweeteners and coloring agents well known to the art. In particular, citric acid is an excellent flavor enhancer for use with the mannitol/sorbitol co-crystal of the invention. Another confectionary using the co-crystalline material is a chocolate composition such as a bar of coating which may be made by a conventional process with cocoa, chocolate liquor, milk powder, vanillin and emulsifier and the mannitol co-crystal of the invention.

Pharmaceutical compositions such as tablets may be made by using the co-crystallized mannitol/ sorbitol the invention as an excipient in combination with a medicinal agent such as vitamin C, aspirin or an antacid. The manufacture of such compositions may be better understood with reference to the following non-limiting examples.

EXAMPLE A

Peppermint flavored tablets may be formulated with the mannitol/sorbitol co-crystal made according to Example 1 as follows: peppermint oil absorbed on a silica gel is compounded with co-crystalline material having a −20/+60 mesh (U.S. sieve series) particle size. After mixing the ingredients in a Patterson-Kelly V-blender, a one gram charge was tableted from a blend containing 96% by weight cocrystals, 1% by weight magnesium stearate and 1% peppermint oil on 2% silica gel. Tablets were made on a Stokes Press using 5/8" FFBE punches employing three tons pressure. Three-quarter inch round tablets and 1" square tablets weighing two grams each were manufactured under three tons pressure using a Key DC16 Instrumented Rotary Press. The hardness of these tablets were measured using a model B-255 Strong Cobb Arner Hardness Tester made by Strong Cobb Arner, Inc. of Cleveland, Ohio, and described in U.S. Pat. No. 2,645,936 issued July 21, 1953. Hardness values of at least about 22 kilograms are obtainable with the 0.625 inch FFBE Punch and above 30 kilograms with the .75 inch and 1 inch punch.

EXAMPLE B

Chocolate flavored sucrose-free coatings were prepared containing single cell protein powder derived from Pseudomonas strain of bacteria grown on a highly purified water soluble methanol substrate as a partial replacement for crystalline sorbitol and co-crystallized mannitol/sorbitol of Example 1. The coatings are prepared in the standard manner by mixing the chocolate liquor, sorbitol co-crystallized mannitol product of Example 1 and Pruteen ® single cell protein with 50% of the cocoa butter lecithin and vannillin. The mass is milled in a three-roll refiner and the flake made thereby is remixed with additional cocoa butter to provide a finished viscosity of 30 Brookfield units. Formulations are listed in Table II.

TABLE II

| CHOCOLATE COATING FORMULATION | | | |
|---|---|---|---|
| | Composition (parts by weight) | | |
| Chocolate Liquor | 70 | 70 | 70 |
| Cocoa Butter | 175 | 175 | 175 |
| Example 1 | 223 | 223 | 139 |
| Pruteen ® Powder | — | 50 | 139 |
| Lecithin | 2.5 | 2.5 | 2.5 |
| Vanillin | 2.0 | 2.0 | 4.0 |

EXAMPLE C

Sucrose-free chocolate is made from the co-crystallized mannitol/sorbitol of Example 1 using a standard formulation. If the co-crystallized product does not have sufficient crystallinity, it will not process well over the rollers as manifested by sticking, flaking and buring of the chocolate paste on the rolls.

The following formulation shown in Table III were processed according to Example B.

TABLE III

| CHOCOLATE FORMULATION | |
|---|---|
| | COMPOSITION (%) |
| Chocolate Liquor | 14.81 |
| Cocoa Butter | 37.04 |
| Example 1 | 47.20 |
| Lecithin | 0.53 |
| Vanillin | 0.42 |
| Aspartame | 0.01 |

Sugarless chewing gum formulas normally comprise a gum base, powdered sorbitol, synthetic sweeteners and plasticizers, sorbitol solution, hydrogenated starch hydrolysate or vegetable solution such as gum arabic. Normally, flavoring and coloring agents are added, as well as humectants such as glycerides.

Chewing gum base is a blend of synthetic and natural products coming within the confines of the U.S. Food, Drug and Cosmetic Law 21 CFR 121.1054. It contains masticatory substances having natural (coagulated or concentrated) latices of vegetable origin. These include Chicle, Perillo, and natural rubber, to name a few, as well as synthetic latices as butadiene styrene, rubber, butyl rubber, paraffin, polyvinyl acetate, polyethylene and others. In addition are included platicizing materials such as glycerol esters of rosin, terpene resins and antioxidants such as butylated hydroxyanisole.

Because of the presence of co-crystallized mannitol and sorbitol crystals, the chewing gum has improved in workability, flavor texture and shelflife.

In general, chewing gum formulations comprise a matrix of a gum base in the range of 20-35% and typically 22-25%; platicizers such as aqueous sorbitol or vegetable synthetic gum 5-25% and typically 10%: glycerine 0-3% and typically 0.5%: powdered mannitol/sorbitol co-crystal gamma polymorph 20-60% and typically 30%; and flavoring ingredients 0.5-2% and typically 1%. Powdered sorbitol is frequently referred to as filler in the trade.

Any suitable manner can be used in forming an intimate mixture of the above described ingredients for manufacturing gum. Usually gum base and artificial sweetening solutions are preheated together in a kettle wherein the ingredients are blended by mixing blades. Desirably, the temperature is maintained at 45° C. or below although slightly higher temperatures can be used in some instances. The mixed gum is maintained at a temperature of about 35°-50° C. and preferably 43° C. during further processing such as rolling, kneading and rolled or extruded to a finished configuration. The gum is then aged as sheets for from 12-72 hours to equilibrate and firm up at which time it is then wrapped. When stored at temperatures between 15°-30° C. and relative humidity is between 33-75% the gum retains functional softness when packaged.

EXAMPLE D

Into a warm sigma blade, steam-heated mixer is added gum base preheated to 65° C. Mannitol/sorbitol co-crystal powder of Example 1 having at least 80% gamma modification is dusted over the blades to prevent sticking. About 1/3 of the powdered ingredients referred to below are then mixed with the warm gum base. The material is mixed for 2 minutes after which is added an additional 1/3 portion of sorbitol powder and gum arabic or hydrogenated starch hydrolysate solution. This is mixed for 2 minutes prior to the addition of the final amount of gamma crystalline mannitol/sorbitol. After 9 minutes mixing, the flavor oil is added and mixed for an additional 3 minutes, a total of 16 minutes.

The material is removed from the mixer and formed into sheets of 0.075 inches in thickness and stored for 24 hours at about 26° C. at 40% R.H. The sheet is cut into strips, wrapped and held at 24° C./40% R.H. and tested for softness over a period of time. Gum formulations appearing in Tables IV, V and VI below and exhibited improved shelf life.

TABLE IV

| FORMULATION | | |
|---|---|---|
| | Grams | % By Weight |
| Gum Base: PALOJA* | 590 | 23.32 |
| Gum Arabic Solution (1 day old) (48%) | 185 | 7.32 |
| Gum Arabic Powder | 50 | 1.98 |
| Example 1 | 950 | 37.55 |
| Mannitol Powder (100%) | 725 | 28.66 |
| Flavor | 30 | 1.19 |
| | 2530 | 100.02 |

*A commercially available product of Dreyfus Corp.

TABLE V

| INGREDIENTS | |
|---|---|
| Gum Base: PALOJA* | 25.04 |
| Sorbitol 70% Aqueous Solution | 20.74 |
| Example 1 | 45.05 |
| Mannitol Powder (100%) | 7.45 |
| Glycerine | 0.52 |
| Flavor | 1.20 |
| | 100.00 |

*A commercially available product of Dreyfus Corp.

TABLE VI

| INGREDIENTS | |
|---|---|
| | % by Weight Based on Total |
| Bubble Gum Base: (LADCO*) | 24.98 |
| Sorbitol 70% Aqueous Solution | 20.70 |
| Example 1 | 52.32 |
| Glycerine | 0.50 |
| Flavor | 1.50 |
| | 100.00 |

*A commercially available product of Dreyfus Corp.

What is claimed is:

1. A co-crystallized mannitol/sorbitol polymorph having an X-ray diffraction pattern of gamma sorbitol containing from 5-35 percent by weight mannitol and a single peak melting point ranging from 90°-100° -C as determined by Differential Scanning Calorimetry.

2. A co-crystallized mannitol/sorbitol polymorph of claim 1 having 8-14 percent by weight mannitol.

3. A co-crystallized mannitol/sorbitol product of claim 1 derived from a dehydrated aqueous solution of sorbitol containing from 7-16 percent mannitol.

4. The co-crystallized mannitol/sorbitol gamma polymorph of claim 1 characterized by crystal widths of about 0.5-1.5 microns as measured on a scanning electron micrograph at 2000× magnification.

5. A tablet comprising the compressed material of claim 1 having a Strong Cobb Arner hardness value of at least about 18-20 kilograms.

6. A confectionary composition comprising the modified gamma-mannitol/sorbitol polymorph of claim 1 and a flavoring agent.

7. The composition of claim 6 wherein said confection is a tablet.

8. The composition of claim 6 wherein said confectionary composition is chewing gum.

9. A confection composition of claim 6 wherein said flavoring agent is chocolate.

10. A composition of claim 9 further comprising single cell protein derived from pseudomonas strain of bacteria grown on a highly purified water soluble methanol substrate.

* * * * *